United States Patent

Effenberger et al.

[11] Patent Number: 5,885,809
[45] Date of Patent: Mar. 23, 1999

[54] METHOD OF PRODUCING (S)-CYANOHYDRINS

[75] Inventors: Franz Effenberger, Stuttgart; Harald Wajant, Leinfelden; Siegfried Förster; Jürgen Roos, both of Stuttgart, all of Germany

[73] Assignee: Degussa Aktiengesellschaft, Frankfurt, Germany

[21] Appl. No.: 796,873

[22] Filed: Feb. 7, 1997

[30] Foreign Application Priority Data

Feb. 9, 1996 [DE] Germany ............ 196 04 715.3

[51] Int. Cl.$^6$ ............ C12P 13/00; C07C 253/06
[52] U.S. Cl. ............ 435/128; 435/136; 435/174; 435/176; 435/280; 558/351
[58] Field of Search ............ 435/128; 558/351

[56] References Cited

U.S. PATENT DOCUMENTS 4,446,232  5/1984  Liotta ............................. 435/7
5,008,192  4/1991  Neidermeyer et al. ............ 435/128

*Primary Examiner*—Johann Richter
*Assistant Examiner*—Ebenezer Sackey
*Attorney, Agent, or Firm*—Pillsbury Madison & Sutro LLP

[57] ABSTRACT

A method for producing (S)-cyanohydrins of general formula

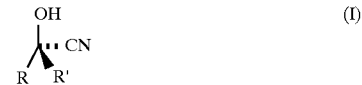

in which R and R' independently represent (1) hydrogen; (2) a substituted or unsubstituted saturated alkyl group which may include amine, imine, hydroxy, $C_1$–$C_8$-alkoxy, halogen, carboxyl, $C_3$–$C_{20}$-cycloalkyl groups and/or a N,O,S-heteroatom-substituted aromatic ring as substituent; (3) a substituted or unsubstituted, singly or multiply unsaturated alkenyl- or alkinyl group which may include one or several amine, imine, hydroxy, $C_1$–$C_8$-alkoxy, halogen, carboxyl, $C_3$–$C_{20}$-cycloalkyl groups and/or one optionally N,O,S-heteroatom-substituted aromatic ring as substituents; (4) a substituted or unsubstituted aromatic or heteroaromatic group. The method includes an enzyme-catalyzed conversion of carbonyl compounds of general formula II

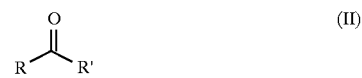

with hydrogen cyanide or a substance supplying hydrogen cyanide or CN- for the conversion in the presence of an amount of an immobilized (S)-oxynitrilase which catalyzes the conversion. The use of nitrocellulose as carrier for the immobilized (S)-oxynitrilase results in a distinct increase of the yield of (S)-cyanohydrin and of the enantiomeric excess compared to the traditional cellulose carrier material.

9 Claims, No Drawings

METHOD OF PRODUCING (S)-CYANOHYDRINS

This application is based on Application No. DE 19604715.3 filed in Germany on Feb. 9, 1996, the entire content of which is incorporated herein by reference.

BACKGROUND OF THE INVENTION

1. Field of the Invention

The invention relates to a method of producing (S)-cyanohydrins with the general formula I

in which the groups R and R' signify, independently of one another:

Hydrogen;

A substituted or unsubstituted, linear or branched, saturated alkyl group with 1 to 18 C atoms which can comprise one or several amine, imine, hydroxy, $C_1$–$C_8$-alkoxy, halogen, carboxyl, $C_3$–$C_{20}$-cycloalkyl groups and/or one optionally N,O,S-heteroatom-substituted aromatic ring with up to 22 C atoms as substituent, which cyclic substituents can be substituted themselves singly or multiply with halogen, hydroxy and/or linear or branched $C_1$–$C_8$-alkyl or $C_2$–$C_8$-alkenyl or $C_2$–$C_8$-alkinyl;

A substituted or unsubstituted, linear or branched, singly or multiply unsaturated alkenyl- or alkinyl group with 2 to 18 C atoms which can comprise one or several amine, imine, hydroxy, $C_1$–$C_8$-alkoxy, halogen, carboxyl, $C_3$–$C_{20}$-cycloalkyl groups and/or one optionally N,O,S-heteroatom-substituted aromatic ring with up to 22 C atoms as substituents, which cyclic substituents can be substituted themselves singly or multiply with halogen, hydroxy and/or linear or branched $C_1$–$C_8$-alkyl or $C_2$–$C_8$-alkenyl or $C_2$–$C_8$-alkinyl;

A substituted or unsubstituted aromatic or heteroaromatic group with 5 to 22 ring atoms in which up to 4 of the ring carbon atoms can be replaced by N, O and/or S and the group can comprise one or several amine, imine, hydroxy, $C_1$–$C_8$-alkoxy, aryloxy, halogen, carboxy and/or linear or branched, saturated or singly or multiply unsaturated alkyl groups with one to 22 C atoms as substituent and at least two of the substituents on the ring can be joined to a cycle, provided that R and R' do not signify hydrogen at the same time, by enzyme-catalyzed conversion of carbonyl compounds of general formula II

in which

R and R' have the meaning indicated for formula I, with hydrogen cyanide or a substance supplying hydrogen cyanide or CN⁻ for the reaction in the presence of an amount of an immobilized (S)-oxynitrilase which catalyses the reaction.

2. Background Information

Starting from chiral cyanohydrins, a plurality of important substance classes of optically active compounds such as e.g. α-amino alcohols, α-hydroxyaldehydes and α-hydroxycarboxylic acids are readily accessible. Methods for producing optically active (S)-cyanohydrins are described in the literature.

The enantioselective addition of trimethylsilyl cyanide in the presence of chiral catalysts plays a significant part in the chemical methods for the synthesis of optically active cyanohydrines.

According to H. Minamikawa, S. Hayakawa, T. Yamada, N. Iwasawa, K. Narasake, Bull. Chem. Soc. Jpn. 61 (1988), 4379 and K. Narasaka, T. Yamada, H. Minamikawa, Chem. Lett. 1987, 2073 the (R)-cyanohydrins are produced starting from a few aliphatic and aromatic aldehydes in good chemical and optical yields (61–93% ee). The authors indicate that the (S)-cyanohydrins are formed when using the corresponding other enantiomer of the catalyst.

According to M. Hayashi, T. Matsuda, N. Oguni, J. Chem. Soc. Chem. Commun. 1990, 1364 titanium tetraisopropanolate with L(+)-diisopropyltartrate or with chiral Schiff bases was used as a further chiral catalyst (M. Hayashi, Y. Miyamoto, T. Inoue, N. Oguni, J. Org. Chem. 58 (1993), 1515). Depending on the catalyst used, both aromatic as well as aliphatic (S)- and (R)-cyanohydrins were produced usually in unsatisfactory enantiomeric excesses of 22–96% ee.

According to E. J. Corey, Z. Wang, Tetrahedron Lett. 34 (1993), 4001, it was possible to obtain a few aliphatic (S)-cyanohydrins by cyanosilylizing in very good chemical and optical yields (ee values up to 95% for heptanal) with a bisoxazoline magnesium complex as chiral catalyst.

Good enantiomeric excesses can also be obtained in the diastereoselective cyanosilylizing of aldehydes acetalized with 2(R),4(R)-pentanediol. According to J. D. Elliot, V. Choi, W. P. Johnson, J. Org. Chem. 48 (1983), 2294 an ee value of 93% at a 97% yield was achieved thereby for (R)-mandelonitrile. If the corresponding 2(S),4(S)-pentanediol is used (S)-cyanohydrin is produced in the same manner.

Even optically active, protected a-amino aldehydes (M. T. Reetz, M. W. Drewes, K. Harms, W. Reif, Tetrahedron Lett. 29 (1988), 3295; J. Herranz, J. Castro-Pichel, T. Gracia-Lopez, Synthesis 1989, 703) and α-hydroxy aldehydes (M. T. Reetz, K. Kesseler, A. Jung, Angew. Chem. 97 (1985), 989) can be converted under Lewis acid-catalysis with trimethylsilyl cyanide or tributyl tin cyanide under moderate to good diastereoselectivity into the corresponding β-amino-α-hydroxy- and α,β-dihydroxynitriles.

A further possibility for synthesizing (S)-cyanohydrins starting from (R)-cyanohydrins is known from F. Effenberger, U. Stelzer, Angew. Chem. 103 (1991), 866 and F. Effenberger, U. Stelzer, Chem. Ber. 126 (1993), 779.

The (R)-cyanohydrins are sulfonylized thereby and then reacted with potassium acetate under $S_N2$ conditions. The acetyl group is removed in the aqueous sour [leaven]. In the case of aliphatic cyanohydrins all stages take place totally free of racemization; racemization occurs in part [at times] in the case of aromatic cyanohydrins. This method can be used especially for those compounds which were not directly accessible since that time on account of the limited substrate spectrum of the (S)-oxynitrilases.

The Mitsunobu reaction also takes place under the inversion of (R)-cyanohydrins (E. Warmerdam, J. Brussee, C. G. Kruse, A. van der Gen, Tetrahedron 49 (1993), 1063).

However, when viewed on the whole it is desirable in every instance to replace the chemical methods by enzyme-catalyzed methods. (R)-cyanohydrins with very differing structure are accessible in very good optical yields via the addition of hydrogen cyanide to aldehydes catalyzed with hydroxynitrile lyase from bitter almonds (PaHNL) (EC 4.1.2.10) (F. Effenberger, Angew. Chem. 1994, 106, 1690–1619). Since the enzyme is also readily accessible in industrial amounts, this method offers the simplest access to (R)-cyanohydrins.

However, the conditions for the enzyme-catalyzed preparation of (S)-cyanohydrins are considerably different. The use of hydroxynitrile lyase from bicolor sorghum (SbHNL) (EC 4.1.2.11) as catalyst has proven to be the most successful (F. Effenberger, B. Hörsch, S. Förster, T. Ziegler, Tetrahedron Lett. 1990, 31, 1249–1252; U. Niedermeyer, M. -R. Kula, Angew. Chem. 1990, 102, 423–425; Angew. Chem. Int. Ed. Engl. 1990, 29, 386–387; M. -R. Kula, U. Niedermeyer, I. M. Stuertz, EP-B 350,908, 1990; DE-B 38 23 866 (Chem. Abstr. 1990, 113, 57462h)), an enzyme which in the meantime can also be obtained from millet seedlings in amounts sufficient for synthetic applications. In addition to the rather difficult accessibility, the substrate spectrum of SbHNL, which is distinctly limited in comparison to PaHNL and accepts only aromatic and heteroaromatic aldehydes as substrates, is a serious disadvantage for the use of this enzyme.

SUMMARY OF THE INVENTION

In view of the state of the art discussed hereinabove, it is an object of the invention to provide a method of the initially mentioned type which permits (S)-cyanohydrins to be obtained in high yield and especially in high enantiomeric purity. It is a further object of the invention to provide an enzymatic method which permits the conversion of as broad a substrate spectrum of initial compounds as possible to the desired target compound.

It is another object of the invention to use enzymes which are available as simply as possible in sufficient amounts and in high activity.

These objects and others not indicated in detail are achieved in a method of the initially cited type by the characterizing feature of claim 1. Advantageous variants of the method are recited in claims which depend from claim 1.

The use of nitrocellulose as carrier for the immobilized (S)-oxynitrilase results in a distinct increase both of the yield of (S)-cyanohydrins as well as of the enantiomeric excess, a result which is not readily foreseeable compared with a traditional cellulose carrier material.

The nitrocellulose used within the scope of the invention as carrier for immobilizing (S)-oxynitrilase is commercially available. It should be expressly pointed out at this point that the designation "nitrocellulose" customarily used in the art is false since nitrocellulose is esters of nitric acid of cellulose, which contain no nitro groups.

Esters of nitric acid of cellulose which are suitable for the invention can display varying degrees of esterification which can be determined via the nitrogen content of the cellulose. The cellulose esters which can be used in accordance with the invention include in particular mononitrate, dinitrate or trinitrate as well as intermediate stages and mixtures of the previously cited substances. Particularly suited nitrocelluloses are those described e.g. in biochemistry as blotting materials (H. Holzhauer in Biochemische Labormethoden, Arbeitsvorschriften und Tabellen [German—Biochemical Laboratory Methods, Work Rules and Tables], Heidelberger Taschenbücher, Springer Verlag, Berlin).

The reaction of carbonyl compounds of general formula II to (S)-cyanohydrins of general formula I catalyzed by (S)-oxynitrilase immobilized on nitrocellulose is advantageously carried out in an organic solvent. The selection of the organic solvent is essentially non-critical; those solvents are especially preferred which dissolve the educts and permit an easy isolation of the products. Appropriate organic solvents are familiar to an expert in the art. Diisopropyl ether is used with particular preference as organic solvent; however, all other ethers customarily used, such as diethyl ether, tetrahydrofurane, etc., or also solvents such as ethyl acetate are used.

It is generally advantageous if the solvents are used in a highly pure form. Absolute freedom from water is not necessary; on the contrary, it is especially advantageous if the organic solvent contains traces of water. As a result of this, it is especially advantageous to use absoluted solvent and to introduce the slight residual amounts of water together with the immobilized enzyme into the reaction.

The reaction in accordance with the invention is carried out in such a manner in an especially preferred method wherein an immobilized enzyme is added which is obtainable by charging nitrocellulose swollen in an acidic buffer with the (S)-oxynitrilase.

In a further development of this method, (S)-oxynitrilase immobilized on nitrocellulose is used, which is obtainable by adding (S)-oxynitrilase to nitrocellulose pre-swollen in aqueous, acidic solution, subsequently filtering off the nitrocellulose charged with (S)-oxynitrilase and centrifuging off excess water from the charged nitrocellulose. The term "pre-swollen nitrocellulose" denotes a carrier material which swells e.g. in a citrate buffer at pH 3.3 for a predetermined time, is then decanted off from the buffer and from which excess liquid components are subsequently centrifuged off. The pre-swollen material is subsequently dried in a vacuum.

It is especially advantageous for the charging of the carrier material with the enzyme if it is carried out at a pH in a range of approximately 3 to 6. The range the range between 3.3 and 5.5 is especially preferred.

According to the invention, (S)-oxynitrilases of various origins can be successfully used.

An especially preferred variant concerns a homomultimer with a native molecular weight of 105–120 kDa for the (S)-oxynitrilase. Furthermore, a preferred (S)-oxynitrilase is characterized in that it is composed as a homomultimer from subunits with a size of 30 kDa.

Manioc is a preferred source for such an enzyme. The pH optimum of the enzyme from manioc [E.C. 4.1.2.37] is in the approximate range of 5.5. This corresponds almost exactly to the pH of 5.3 present in the cell. Investigations for the temperature optimum of the enzyme from manioc show that the activity rises steadily until 40° C. and remains almost constant between 40 and 50° C.

A further source for an (S)-oxynitrilase which can be used in accordance with the invention is *Hevea brasiliensis* (rubber tree). Even this (S)-oxynitrilase has a very broad substrate spectrum and converts a plurality of aliphatic and aromatic carbonyl compounds.

Finally, in addition to the enzymes from *Manihot esculenta* and *Hevea brasiliensis* every (S)-oxynitrilase serologically related to them can also be used. A description of (S)-oxynitrilase isolated from *Manihot esculenta* is located e.g. in Plant Science 108 (1995) 1–11. A description of (S)-oxynitrilase isolated from *Hevea brasiliensis* is indicated e.g. in Plant Science 1 15 (1996) 25–31.

In addition to the sources already named, an (S)-oxynitrilase which can be used within the scope of the invention is readily accessible in industrial amounts by using recombinant (S)-oxynitrilase e.g. from *Manihot esculenta*. It is possible, by obtaining the (S)-oxynitrilase from *Manihot esculenta* by genetic engineering, to make an enzyme accessible which on the one hand displays a broad substrate spectrum for obtaining (S)-cyanohydrins and on the other hand can be made accessible in a simple manner and in sufficient amounts based on expression cloning.

In particular, even the recombinant enzyme catalyzes the enantioselective addition of hydrogen cyanide to a plurality of aldehydes and ketones. Hydrogen cyanide can be used for this purpose in direct form or in the form of a precursor which releases hydrogen cyanide under the reaction conditions. An enantioselective addition of HCN to ketones catalyzed by enzymes has been demonstrated in the past for the hydroxynitrile lyase from bitter almonds (PaHNL) and for the hydroxynitrile lyase from *Linum usitatissimum*, both of which catalyze the formation of (R)-keto cyanohydrins. A synthesis of (S)-keto cyanohydrins with an (S)-hydroxynitrile lyase has not yet been described. (S)-keto cyanohydrins were recently able to be produced by transcyanization from racemic keto cyanohydrins with the (R)-hydroxynitrile lyase PaHNL. It is remarkable that the optical yields in the reactions of alkylmethylketone increase as the size of the alkyl group increases. Whereas branches in the β position of the alkyl substituent have no disadvantageous influence on the enantioselectivity, the optical yields decrease sharply given a strong steric hindrance in the vicinal position to the carbonyl group. The hydroxynitrile lyase from Manihot esculenta therewith displays an exceedingly broad substrate spectrum and an aromatic ketone like acetophenone is readily accepted as substrate.

DETAILED DESCRIPTION OF THE INVENTION

The invention is explained in more detail below using exemplary embodiments.

Overexpression of MeHNL in *E. coli*

The coding region of the MeHNL gene was amplified from oligo(dT) primed cDNA with PCR (sense primer: GCA GGG CCG GAT CCC ATT TCC AAA ATG GTA ACT GCA CA; antisense primer: GCA GGG CCG GAT CCA CAC AAC GTG GAA CTC TCC CAT ATT; underlined ranges correspond to position 16–39 and 933–910 of the cCNA sequence of MeHNL) and cloned in the correct reading frame into the pQE4 expression vector (Quiagen). The expression plasmid pQE4-MeHNLwt obtained in this manner was transfixed for MeHNL expression in *E. coli*-M15 [pREP4]cells (M15-MeHNL).

An 8 L culture was inoculated with 2 mL of a culture of M15-MeHNL approximately 12 h old in LB medium with ampicillin (100 μg mL$^{-1}$) and kanamycin (25 μg mL$^-$). This culture was used after approximately 12 h cultivation at 37° C. for inoculating a 100 L fermenter (Bioengineering). The M15-MeHNL cells were cultivated 1 h at 30° C. and a further 3.5 h after induction of the expression with isopropyl-β-D-thiogalactoside (IPTG) (final concentration 1 mM). The cells were then concentrated to small volume by cross-flow concentration (Maxisette system) on a 0.3 μm membrane (0.46 m$^2$) (Filtron) to approximately 7.5 L. In order to separate residual LB medium the cells were centrifuged 10 min at 10,000×g. The cell pellet obtained was re-suspended in 2 L sodium acetate buffer (50 mM, pH 5.4) and the cells macerated by high-pressure homogenization (500 bar, 3 cycles, Rannie-APV MiniLab). In order to remove chromosomal DNA the raw lysate (total amount of HNL 40,000 U, spec. activity 2.8 U mg$^-$) was digested 1 h at room temperature with benzonase (Merck) (final concentration 5000 U$^{-1}$). After 1 h of centrifuging at 130,000×g the MeHNL was enriched by anion exchange chromatography to a specific activity of 12 U mg$^{-1}$). For this a Q-sepharose FF 100/1200 column was equilibrated with 200 mM sodium acetate buffer, pH 5.7 (buffer A) and the bound proteins eluted with 7200 mL of a linear gradient of 0–1M NaCl in buffer A with a flow rate of 50 mL min$^{-1}$. MeHNL elutes after 450 mL salt gradient.

Reagents a) 20 mM sodium acetate buffer:

01 ml acetic acid (10 mmoles) in 500 ml sterile water adjusted with concentrated sodium hydroxide solution to the desired pH. 01M sodium acetate buffer pH 5.4:

21 ml acetic acid (50 mmoles) in 497 ml sterile water adjusted with concentrated sodium hydroxide solution to pH 5.4.

20 mM sodium citrate buffer with pH 3.3:

21 g citric acid monohydrate (10 mmoles) dissolved in 500 ml sterile water and adjusted with concentrated sodium hydroxide solution to pH 3.3.

10 % acetone cyanohydrin solution in 0.1M citric acid:

1 ml freshly distilled acetone cyanohydrin is added to 9 ml of a citric acid solution (0.21 g citric acid monohydrate in 10 ml sterile water).

a) Solvent:

Diisopropyl ether, diethyl ether: Distillation over sodium wire

Methylene chloride: Distillation over calcium hydride

Pyridine: Distillation over potassium hydroxide

Acetane hydride: Distillation a) Educts:

The initial compounds were obtained from the cited companies or produced according to Autorenkollektiv, Organikum, VEB Verlag der Wissenschaften, Berlin, 16$^{th}$ edition (1986):

Aldrich Chemie, Steinheim [city]

Fluka Chemika, Buchs (CH)

Janssen Chimica, Belgium

Merck-Suchhardt, Hohenbrunn

The aldehydes and ketones were used freshly distilled.

Racemic cyanohydrins 3, 5: According to Autorenkollektiv, Organikum, VEB Verlag der Wissenschaften, Berlin, 16$^{th}$ edition (1986)

anhydrous hydrogen cyanide (2): by dropping concentrated sodium cyanide solution into sulfuric acid; the hydrogen cyanide being produced is condensed at −12° C. and stored in dry ice.

(S)-/(R)-MTPA-Cl: According to J. A. Dale, D. L. Dull, H. S. Mosher, J. Org. Chem. 34 (1969), 2543

Spectroquant® 14800 CN: Merck, Darmstadt a) Carrier materials

Avicel cellulose: Merck, Darmstadt

P100PSC cellulose: Degussa, Frankfurt

Nitrocellulose: blotting membrane; Schleicher & Schuell, Dassel a) Isolation of (S)-oxynitrilase [E.C. 4.1.2.37]:

The isolation of (S)-oxynitrilase takes place either from freeze-dried manioc leaves from Columbia, or from recombinant protein from *E. coli* by ion exchange chromatography.

Enzyme-catalyzed preparation of (S)-cyanohydrins 50 mg carrier (nitrocellulose) is allowed-to swell 30 min in 3 mL 0.02M sodium citrate buffer. After decanting, centrifuging (30 min, 5700×g) and 5 h drying in a high vacuum the amount of conc. MeHNL solution (099 U mL$^{-1}$) indicated in the tables is added dropwise and the mixture is centrifuged after 15 min (at −5° C., 30 min 3650×g).

The enzyme-charged carrier is transferred into a flask, 5 mL diisopropyl ether, 0.3–0.4 mmole 1 or 3 and 100 μl (2.6 mmoles) HCN are added and the mixture agitated at room temperature for the time indicated in the tables. The carrier is removed by suction, a wash with diethyl ether carried out, the combined filtrates dried and the solvent and non-reacted educt (1a–g, 3a–f) distilled off. The aldehyde cyanohydrins (S)-2a–j (table 1) and the ketone cyanohydrins (S)-4a–f (table 2) accumulate in pure form. In the case of the compounds (S)-2k–o and (S)-4g the purification takes place via a derivatization as acetates and trimethylsilyl ether, during which the yields determined by NMR spectroscopy (tables 1, 2) are corroborated.

TABLE 1

|   | Aldehydes 1 | Enzymes | (S)-cyanohydrins 2 | | |
|---|---|---|---|---|---|
|   | R | (U/mmole 1) | t (h) | yield (%) (a) | 33(%) (b) |
| a | $C_2H_5$ | 34 | 4.3 | 86 | 91 |
| b | $nC_4H_9$ | 61 | 4.0 | 100 | 91 |
| c | $(H_3C)_2CH$ | 32 | 6.5 | 91 | 95 |
| d | $(H_3C)_3C$ | 39 | 8.8 | 80 | 94 |
| e | $H_2C=CH$ | 119 | 0.5 | 100 | 47 |
| f | $H_3CCH=CH$ | 145 | 1.0 | 100 | 92 |
| g | $E\text{-}H_3C(CH_2)_2CH=CH$ | 130 | 3.0 | 82 | 97 |
| h | $cC_6H_{11}$ | 70 | 5.3 | 100 | 92 |
| i | $C_6H_5$ | 58 | 7.0 | 100 | 98 |
| j | $2\text{-}Cl\text{—}C_6H_4$ | 107 | 8.7 | 100 | 92 |
| k | $4\text{-}H_3CO\text{—}C_6H_4$ | 130 | 9.5 | 82 | 98 |
| l | $3,4\text{-}CH_2O_2\text{—}C_6H_3$ | 110 | 10.3 | 84 | 86 |
| m | 2-Thienyl | 134 | 6.0 | 85 | 96 |
| n | 3-Thienyl | 149 | 4.0 | 98 | 98 |
| o | 3-Furyl | 141 | 6.5 | 98 | 92 |

(a) Yield for 2h-o determined by $^1$H-NMR spectroscopy.
(b) Determined by gas chromatography on β-cyclodextrine phases after acetylation with acetic anhydride [1.9]

Scheme 1:
(S)-cyanohydrins (S)-2 by MeHNL-catalyzed addition of HCN on aldehydes 1 in diisopropyl ether as solvent

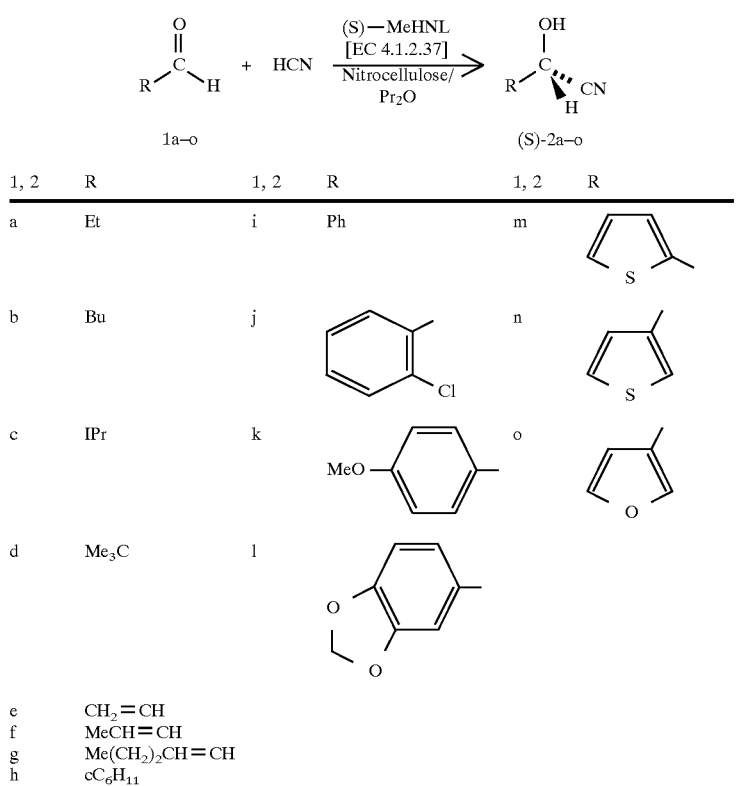

| 1, 2 | R | 1, 2 | R | 1, 2 | R |
|---|---|---|---|---|---|
| a | Et | i | Ph | m | (2-thienyl) |
| b | Bu | j | (2-chlorophenyl) | n | (3-thienyl) |
| c | IPr | k | (4-methoxyphenyl) | o | (3-furyl) |
| d | $Me_3C$ | l | (3,4-methylenedioxyphenyl) | | |
| e | $CH_2=CH$ | | | | |
| f | $MeCH=CH$ | | | | |
| g | $Me(CH_2)_2CH=CH$ | | | | |
| h | $cC_6H_{11}$ | | | | |

Scheme 2:
(S)-ketone cyanohydrins (S)-4 by MeHNL-catalyzed addition of HCN on methylketones 3 in diisopropyl ether

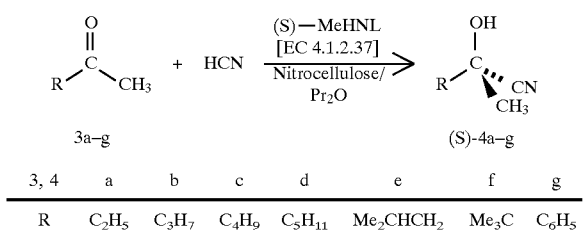

| 3, 4 | a | b | c | d | e | f | g |
|---|---|---|---|---|---|---|---|
| R | $C_2H_5$ | $C_3H_7$ | $C_4H_9$ | $C_5H_{11}$ | $Me_2CHCH_2$ | $Me_3C$ | $C_6H_5$ |

TABLE 2

| Ketones 3 | | Enzyme | (S)-ketone cyanohydrins 4 | | |
|---|---|---|---|---|---|
| | R | (U/mmole 3) | t(h) | yield (%) | ee (%) (a) |
| a | $C_2H_5$ | 53 | 4.0 | 91 | 18 |
| b | $nC_3H_7$ | 123 | 0.5 | 36 | 69 |
| c | $nC_4H_9$ | 123 | 0.5 | 58 | 80 |
| d | $nC_5H_{11}$ | 126 | 2.0 | 39 | 92 |
| e | $(H_3C)_2CHCH_2$ | 107 | 0.7 | 69 | 91 |
| f | $(H_3C)_3C$ | 107 | 0.8 | 81 | 28 |
| g | $C_6H_5$ | 112 | 7.0 | 13 [b] | 78 |

(a) Determined by gas chromatography on β-cyclodextrine phases after acetylation with acetic anhydride, saponification to carboxylic acid and subsequent esterification to the methyl ester or via diastereomeric (S)-MTPA esters [1,9]
(b) Yield determined by $^1$H-NMR spectroscopy.

Carrier variation

In order to bring out the advantages over the previously used cellulose P100PSC the carriers are compared to each other using the example of the conversion of isobutyraldehyde (1e).

TABLE 3

Conversions of isobutyraldehyde (1c) with (S)-oxynitrilase and hydrogen cyanide (2) to (S)-cyanohydrin 2c with variation of the carrier material and associated blind tests

| Carrier | Amount of enzyme U/mmole 1e[1] | centrifuged off (%) | Reaction time (h) | Blind test[2] yield (%) | (S)-cyanohydrin 2c yield (%) | ee (S)-2c (%) |
|---|---|---|---|---|---|---|
| 200 mg P100PSC swollen in NaOAc pH 3.3 | 56 | —[3] | 7.5 | 71 | 54 | 49 |
| 150 mg P100PSC swollen in NaOAc pH 3.3, centrifuged off | 32 | 75 | 6.5 | 19 | 53 | 63 |
| 50 mg non-swollen nitrocellulose centrifuged off | 32 | 1 | 6.5 | 96 | 90 | 86 |
| 50 mg nitrocellulose swollen in cit. Buffer pH 3.3, centrifuged off | 32 | 2 | 6.5 | 17 | 91 | 95 |

[1] Amount of enzyme used before centrifuging off
[2] Instead of the enzyme solution an appropriate amount of a 20 mM sodium acetate buffer pH 5.4 is used
[3] Was not centrifuged off If the two batches with cellulose P100PSC are observed, it is apparent that 75% of the enzyme goes into the centrifugate during the centrifuging off. The enantiomeric excess therefore rises only slightly in spite of a very much lower water content. In contrast thereto the (S)-oxynitrilase remains almost quantitatively on the nitrocellulose during centrifuging. Thus, only water is centrifuged off here on account of the high affinity to proteins. The low water content is decisive for the distinct rise of the optical yields.

The best results regarding the chemical and optical yields are achieved with nitrocellulose pre-swollen in sodium citrate buffer pH 3.3 which nitrocellulose is subsequently centrifuged off. The two advantages of low water amount and of low pH are combined here. This is reflected both in the very high enantiomeric excess for the cyanohydrin 2c and also in the relatively low yield of the blind test.

TABLE 4

Comparison of the carriers when using a concentrated enzyme solution (900 U/ml)

| Substrate | Reaction time (h) | P100PSC yield/ conversion ee (%) | | Nitrocellulose yield/ conversion ee (%) | |
|---|---|---|---|---|---|
| Heptanal | 9 | 69 | 79 | 61 | 79 |
| Acrolein | 1 | 29 | 41 | 70 | 56 |
| Furfural | 9 | 68 | 89 | 84 | 97 |
| 3-methoxy-benzaldehyde | 8.5 | 25 | 92 | 32 | 9 |

What is claimed is:
1. A method of producing (S)-cyanohydrins of formula I

wherein the groups R and R' signify, independently of one another:
Hydrogen;
A substituted or unsubstituted, linear or branched, saturated alkyl group with 1 to 18 C atoms wherein the substituents are one or several amino, imino, hydroxy, $C_1$–$C_8$-alkoxy, halogen, carboxyl, $C_3$–$C_{20}$-cycloalkyl groups and/or one optionally N,O,S-heteroatomsubstituted aromatic ring with up to 22 C atoms as substituent, which cyclic substituents may be substituted themselves singly or multiply with halogen, hydroxy and/or linear or branched $C_1$–$C_8$-alkyl or $C_2$–$C_8$-alkenyl or $C_2$–$C_8$-alkinyl;

A substituted or unsubstituted, linear or branched, singly or multiply unsaturated alkenyl- or alkinyl group with 2 to 18 C atoms wherein the substituents are one or several amino, imino, hydroxy, $C_1$–$C_8$-alkoxy, halogen, carboxyl, $C_3$–$C_{20}$-cycloalkyl groups and/or one optionally N,O,S-heteroatom-substituted aromatic ring with up to 22 C atoms as substituents, which cyclic substituents may be substituted themselves singly or multiply with halogen, hydroxy and/or linear or branched $C_1$–$C_8$-alkyl or $C_2$–$C_8$-alkenyl or $C_2$–$C_8$-alkinyl;

A substituted or unsubstituted aromatic or heteroaromatic group with 5 to 22 ring atoms in which up to 4 of the ring carbon atoms may be replaced by N, O and/or S wherein the substituents are one or several amino, imino, hydroxy, $C_1$–$C_8$-alkoxy, aryloxy, halogen, carboxy and/or linear or branched, saturated or singly or multiply unsaturated alkyl groups with one to 22 C atoms as substituent and at least two of the substituents on the ring may be joined to a cycle, provided that R and R' are not both hydrogen, by enzyme-catalyzed conversion of carbonyl compounds of general formula II

 (II)

in which

R and R' have the meaning indicated for formula I, with hydrogen cyanide or a substance supplying hydrogen cyanide or CN⁻ for the reaction in the presence of an amount of an immobilized (S)-oxynitrilase which catalyses the reaction, wherein nitrocellulose is used as carrier for the immobilized (S)-oxynitrilase and the reaction is carried out in an organic solvent.

2. The method according to claim 1, wherein the organic solvent is diisopropyl ether.

3. The method according to claim 1, or 2, wherein the organic solvent contains traces of water.

4. The method according to claim 1 or 2, wherein the enzyme has been immobilized by charging nitrocellulose swollen in an acidic buffer with (S)-oxynitrilase.

5. The method according to claim 4, wherein said enzyme is (S)-oxynitrilase immobilized on nitrocellulose, which has been obtained by the steps of adding (S)-oxynitrilase to nitrocellulose pre-swollen in aqueous, acidic solution;

filtering off nitrocellulose charged with (S)-oxynitrilase; and centrifuging off excess water from the charged nitrocellulose.

6. The method according to claim 6, wherein the charging of the nitrocellulose is carried out at a pH in a range of approximately 3–6.

7. The method according to claim 4 wherein the enzyme is (S)-oxynitrilase composed as a homomultimer of subunits 30 kDa in size.

8. The method according to claim 4, wherein an (S)-oxynitrilase isolated from Manihot esculenta or Hevea brasiliensis or an (S)-oxynitrilase serologically related to said (S)-oxynitrilase is used.

9. The method according to claim 8 wherein recombinant (S)-oxynitrilase from Manihot esculenta is used.

* * * * *

UNITED STATES PATENT AND TRADEMARK OFFICE
CERTIFICATE OF CORRECTION

PATENT NO. : 5,885,809
DATED : March 23, 1999
INVENTOR(S) : EFFENBERGER et al.

It is certified that error appears in the above-indentified patent and that said Letters Patent is hereby corrected as shown below:

On the title page item [22], should read --Feb. 10, 1997--.

Signed and Sealed this

Ninth Day of November, 1999

Attest:

Q. TODD DICKINSON

Attesting Officer

Acting Commissioner of Patents and Trademarks